(12) United States Patent
Okamura

(10) Patent No.: US 12,180,310 B2
(45) Date of Patent: Dec. 31, 2024

(54) SILOXANE AND A METHOD FOR PREPARING THE SAME

(71) Applicant: Shin-Etsu Chemical Co., Ltd., Tokyo (JP)

(72) Inventor: Kaoru Okamura, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 614 days.

(21) Appl. No.: 17/616,388

(22) PCT Filed: May 26, 2020

(86) PCT No.: PCT/JP2020/020739
§ 371 (c)(1),
(2) Date: Dec. 3, 2021

(87) PCT Pub. No.: WO2020/246313
PCT Pub. Date: Dec. 10, 2020

(65) Prior Publication Data
US 2022/0332863 A1  Oct. 20, 2022

(30) Foreign Application Priority Data
Jun. 6, 2019 (JP) ................................ 2019-106366

(51) Int. Cl.
C08F 130/08 (2006.01)
C07F 7/08 (2006.01)
C08F 120/68 (2006.01)

(52) U.S. Cl.
CPC ................................ C08F 120/68 (2013.01)

(58) Field of Classification Search
None
See application file for complete search history.

(56) References Cited

U.S. PATENT DOCUMENTS

| 4,139,692 A | 2/1979 | Tanaka et al. |
| 11,919,987 B2* | 3/2024 | Okamura .................. C08J 3/075 |
| 2008/0004383 A1 | 1/2008 | Nakamura et al. |
| 2009/0005528 A1* | 1/2009 | Fujisawa ................ G02B 1/043 556/400 |
| 2020/0131316 A1* | 4/2020 | Iguchi .................... C08G 77/08 |

FOREIGN PATENT DOCUMENTS

| EP | 3845571 A1 | 7/2021 |
| JP | S5455455 A | 5/1979 |
| JP | S5622325 A | 3/1981 |
| JP | 2004182724 A | 7/2004 |
| JP | 2009542674 A | 12/2009 |
| JP | 2013231046 A | 11/2013 |
| WO | 2020045225 A1 | 3/2020 |

OTHER PUBLICATIONS

English translation of International Search Report corresponding to International Patent Application No. PCT/JP2020/020739 (2 pages) (mailed Aug. 11, 2020).
Extended European Search Report corresponding to European Patent Application No. 20818839.1 (5 pages) (dated Apr. 21, 2023).
"Soluble Silicone Prepolymers", Database Reaxys, Toray Industries Inc; Johnson & Johnson Inc. XP093039103, Database accession No. XRN = 37035162 (2 pages).

* cited by examiner

*Primary Examiner* — Michael J Feely
(74) *Attorney, Agent, or Firm* — Myers Bigel, P.A.

(57) ABSTRACT

A purpose of the present invention is to provide a siloxane suitable for preparing a medical material and a method for preparing the compound. The present invention provides a siloxane represented by the formula (1), wherein $R^1$ is a hydrogen atom or a methyl group, $R^2$ is a monovalent hydrocarbon group having 1 to 6 carbon atoms, L is a divalent hydrocarbon group which has 2 to 10 carbon atoms and may have one or more ether bonds, and A is a (poly) siloxane group represented by the formula (2) or (3), wherein n is an integer of 1 to 100, a is an integer of 0 to 10, b is an integer of 0 to 10, and c is an integer of 0 to 10, provided that a+b+c is 2 or more, and R is, independently of each other, a monovalent hydrocarbon group having 1 to 10 carbon atoms. The present invention further provides a method for preparing the siloxane, a polymer comprising recurring units derived from the siloxane, and a medical material, particularly an ophthalmic device, comprising the aforesaid polymer.

20 Claims, No Drawings

SILOXANE AND A METHOD FOR PREPARING THE SAME

TECHNICAL FIELD

The present invention relates to a siloxane. Specifically, the invention provides a siloxane suitable for preparing a medical material and a method for preparing the siloxane.

BACKGROUND OF THE INVENTION

Monomers comprising siloxane units are known as a compound used for preparing medical materials including ophthalmic devices. For example, 3-[tris(trimethylsiloxy)silyl]propyl methacrylate (TRIS) is widely known as a monomer for ophthalmic devices. A polymer obtained by the copolymerization of TRIS with a hydrophilic monomer, N,N-dimethylacrylamide or N-vinyl-2-pyrrolidone, have useful characteristics such as high oxygen permeability. The siloxane monomer which is highly hydrophobic does not have sufficient compatibility with such a hydrophilic monomer. Therefore, in the preparation of a hydrogel prepared from these for a medical material, phase separation, so that the hydrogel is cloudy.

Patent Literatures 1, 2, 3 and 4 disclose siloxanes which are represented by the following formula (a), (a'), (b) or (b') and has a glycerol methacrylate moiety.

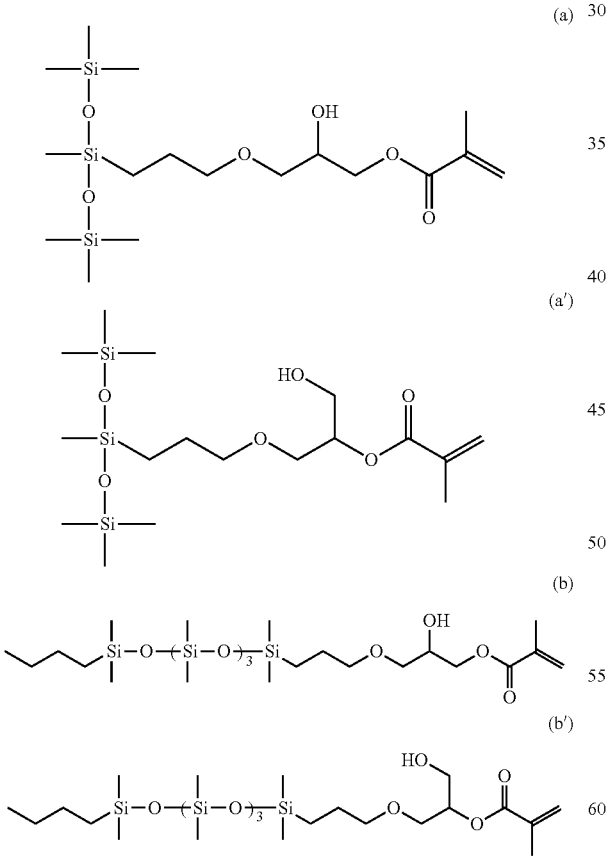

The aforesaid compounds have a hydroxyl group and, accordingly, good hydrophilicity. Therefore, they have an advantage of excellent compatibility with a hydrophilic monomer.

PRIOR LITERATURES

Patent Literatures

Patent Literature 1: Japanese Patent Application Laid-Open No. Sho54 (1979)-55455

Patent Literature 2: Japanese Patent Application Laid-Open No. Sho 56(1981)-22325

Patent Literature 3: Japanese Patent Application Laid-Open No. 2004-182724

Patent Literature 4: Japanese Patent Application Laid-Open No. 2013-231046

SUMMARY OF THE INVENTION

Problems to be Solved by the Invention

When a hydrogel is prepared using a compound having a primary secondary hydroxyl group at a position where the aforesaid (poly)siloxane and a polymerizable group are linked with each other, the highly reactive hydroxyl group may cause an undesirable result. For example, a radical may bond to the hydroxyl group of the compound to form a hydroxy radical, which may cause crosslinked structure. This may cause an unexpected increase in hardness and decrease in hydrophilicity due to the decreased hydroxyl group amount. Thus, the conventional siloxane compounds cannot provide a medical material having useful hydrophilicity and sufficient strength. Therefore, a compound and a composition which overcome such defects are still desired.

A purpose of the present invention is to provide a siloxane suitable for preparing a medical material and a method for preparing the compound.

Means for Solving the Problems

The present inventor conducted keen researches to solve the aforesaid problems and has found that a (poly)siloxane monomer having a (poly)siloxane structure at its end and having a tertiary hydroxyl group at a position where the (poly)siloxane structure and a polymerizable group are linked with each other is excellent in compatibility with another hydrophilic monomer and does not cause unexpected formation of a crosslinked structure in a (co)polymer of the (poly)siloxane monomer and the hydrophilic monomer.

That is, the present invention provides a siloxane represented by the following formula (1):

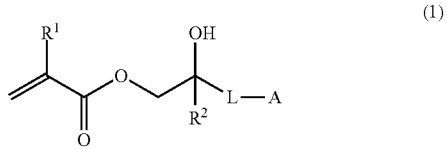

wherein $R^1$ is a hydrogen atom or a methyl group, $R^2$ is a monovalent hydrocarbon group having 1 to 6 carbon atoms, L is a divalent hydrocarbon group which has 2 to 10 carbon atoms and may have one or more ether bonds, and A is a group represented by the following formula (2) or (3):

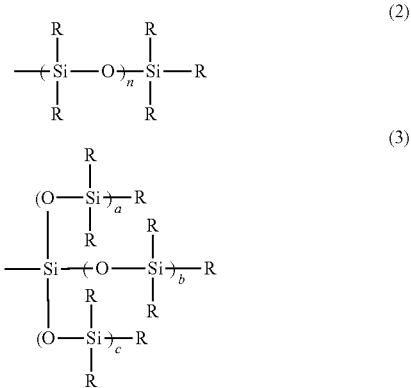

wherein n is an integer of 1 to 100, a is an integer of 0 to 10, b is an integer of 0 to 10, and c is an integer of 0 to 10, provided that a+b+c is 2 or more, and R is, independently of each other, a monovalent hydrocarbon group having 1 to 10 carbon atoms.

The present invention further provides a method for preparing the aforesaid siloxane, a polymer comprising recurring units derived from the aforesaid siloxane, and a medical material, particularly an ophthalmic device, comprising the aforesaid polymer.

Effects of the Invention

The siloxane of the present invention has a tertiary hydroxyl group and thereby is excellent in compatibility with a hydrophilic monomer. A (co)polymer having recurring units derived from the siloxane has a preferable strength. The siloxane of the present invention is useful as a monomer for preparing a medical material.

DETAILED DESCRIPTION OF THE INVENTION

The siloxane of the present invention will be described below in detail.

The present invention provides a siloxane represented by the aforesaid formula (1). The present siloxane is characterized in that the siloxane has a (poly)siloxane structure indicated by A at the terminal, a (meth)acryloyl group at another terminal, and a tertiary hydroxyl group on a linking part between the (poly)siloxane and the (meth)acryloyl group. The hydrophilic hydroxyl group is tertiary, whereby a side reaction is prevented in the preparation of the present siloxane. On account of these characteristics, the siloxane provides a (co)polymer having a recurring unit derived from the present siloxane and having a preferable strength, while keeping its compatibility with a hydrophilic monomer.

In the aforesaid formula (1), $R^1$ is a hydrogen atom or a methyl group, preferably a methyl group.

In the aforesaid formula (1), $R^2$ is a monovalent hydrocarbon group having 1 to 6 carbon atoms. Examples of the monovalent hydrocarbon groups include alkyl groups such as methyl, ethyl, propyl, n-butyl, t-butyl, pentyl, and hexyl groups; cycloalkyl groups such as cyclopentyl and cyclohexyl groups; and aryl groups such as a phenyl group. $R^2$ is preferably an alkyl group having 1 to 4 carbon atoms, more preferably a methyl group.

In the aforesaid formula (1), L is a divalent hydrocarbon group which has 2 to 10 carbon atoms and may have one or more ether bonds, preferably a divalent hydrocarbon group having 4 to 10 carbon atoms. Examples of the aforesaid divalent hydrocarbon group include ethylene, 1,3-propylene, 1-methylpropylene, 1,1-dimethylpropylene, 2-methylpropylene, 1,2-dimethylpropylene, 1,1,2-trimethylpropylene, 1,4-butylene, 2-methyl-1,4-butylene, 2,2-dimethyl-1,4-butylene, 3-methyl-1,4-butylene, 2,2-dimethyl-1,4-butylene, 2,3-dimethyl-1,4-butylene, 2,2,3-trimethyl-1,4-butylene, 1,5-pentylene, 1,6-hexanylene, 1,7-heptanylene, 1,8-octanylene, 1,9-nonanylene and 1,10-decanylene.

Examples of the divalent hydrocarbon group which has 2 to 10, preferably 4 to 10 carbon atoms, and has one or more ether bonds include (poly)alkylene oxide groups such as (poly)ethylene oxide, (poly)propylene oxide, and (poly)ethylene-propylene oxide groups. Preferred is a group represented by the following formula (4):

wherein p is an integer of 1 to 2; q is an integer of 1 to 4, preferably an integer of 2 to 4, more preferably 2; the site marked with * is bonded to the carbon atom in the formula (1) and the site marked with ** is bonded to A in the formula (1).

The group represented by the aforesaid formula (4) is preferably $-CH_2OC_3H_6-$ or $-CH_2OC_2H_4OC_3H_6-$.

"A" is a polysiloxane group represented by the aforesaid formula (2) or (3), n is an integer of 1 to 100, a is an integer of 0 to 10, b is an integer of 0 to 10, and c is an integer of 0 to 10, provided that a+b+c is 2 or more. Preferably, n is an integer of 2 to 20. In the formula (3), it is preferred that a is 1, b is 1, and c is 0.

R is, independently of each other, a monovalent hydrocarbon group having 1 to 10 carbon atoms, preferably 1 to 6 carbon atoms. Examples of the monovalent hydrocarbon group include alkyl groups such as methyl, ethyl, propyl, n-butyl, t-butyl, pentyl, hexyl, heptyl, octyl, nonyl, and decyl groups; cycloalkyl groups such as cyclopentyl and cyclohexyl groups; and aryl groups such as phenyl and tolyl groups. R is preferably an alkyl group having 1 to 10 carbon atoms, more preferably 1 to 6 carbon atoms, or a phenyl group; and more preferably a methyl, n-butyl, or t-butyl group.

A method for preparing the siloxane represented by the aforesaid formula (1) will be described below.

The preparation method of the present invention comprises a step of hydrosilylation, wherein a compound represented by the following formula (5) and having unsaturated groups at the terminals thereof:

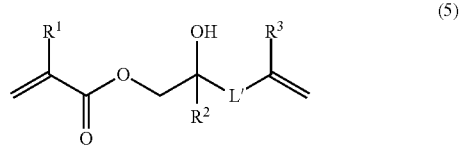

wherein $R^1$ and $R^2$ are as described above, $R^3$ is a hydrogen atom or a methyl group, and L' is a single bond or a divalent hydrocarbon group which has 1 to 8 carbon atoms and may have one or more ether bonds, is reacted with a hydrogen siloxane compound represented by the following formula (6) or (7):

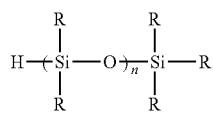
(6)

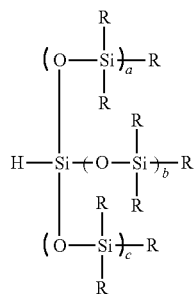
(7)

wherein R, n, a, b and c are as described above, to obtain the siloxane represented by the aforesaid formula (1).

The preparation method of the present invention is characterized in that the compound represented by the formula (5) has an unsaturated bond at the terminal thereof and a tertiary hydroxyl group. In the present preparation method, because the hydroxyl group of the raw material compound represented by the aforesaid formula (5) is tertiary, any undesirable side reaction by a hydroxyl group is suppressed in the hydrosilylation reaction. Therefore, the obtained siloxane has high purity.

In the aforesaid formula (5), $R^3$ is a hydrogen atom or a methyl group, preferably a hydrogen atom.

In the aforesaid formula (5), L' is a single bond or a divalent hydrocarbon group which has 1 to 8 carbon atoms and may have one or more ether bonds, preferably a divalent hydrocarbon group having 2 to 8 carbon atoms and having one or more ether bonds.

Examples of the divalent hydrocarbon group having 1 to 8 carbon atoms include methylene and the aforesaid divalent hydrocarbon groups. Examples of the group having one or more ether bonds include (poly)alkyleneoxide groups such as (poly)ethylene oxide, (poly)propylene oxide, and (poly)ethylene-propylene oxide groups. Particularly, a group represented by the following formula (4') or (4") is preferred.

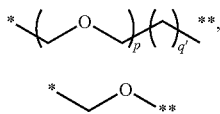
(4')
(4")

wherein p is an integer of 1 to 2, q' is an integer of 0 to 2, preferably 0 or 1, more preferably 0; and the site marked with * is bonded to the carbon atom in the formula (5) and the site marked with ** is bonded to A in the formula (1). Thus, the divalent hydrocarbon group represented by the formula (4') or (4") is preferably —$CH_2OCH_2$— or —$CH_2OC_2H_4OCH_2$—.

The hydrosilylation-reaction may be done in any known method. For example, 1 molar equivalent of the hydrogen siloxane compound represented by the formula (6) or (7) and 1 molar equivalent or more of the unsaturated compound represented by the formula (5) may be subjected to the reaction. A reaction temperature is not particularly limited, and is preferably a temperature not exceeding a boiling temperature of a solvent to be used. For example, the reaction temperature is preferably from about 0° C. to about 120° C. The reaction may be done in the presence of a solvent, a hydrosilylation catalyst and a stabilizer. Any known solvent, hydrosilylation catalyst and stabilizer may be used.

In the aforesaid reaction, the amount of the unsaturated compound is preferably 1 molar equivalent or more, per mole of the hydrogen siloxane compound. The amount of the unsaturated compound is more preferably 1.0 to 3.0 molar equivalents, still more preferably 1.1 to 2.0 molar equivalent, particularly preferably 1.2 to 1.5 molar equivalents. When 1 molar equivalent or more of the unsaturated compound is added, an amount of the remaining hydrogen siloxane compound and a side reaction are suppressed. Although the upper limit of the amount of the unsaturated compound is not limited, too large amount is not preferred from the standpoint of a yield and economy.

The hydrosilylation catalyst is, for example, a noble metal catalyst, particularly a platinum catalyst derived from chloroplatinic acid. Preferably, the chlorine ions of chloroplatinic acid are neutralized with sodium bicarbonate to improve stability of the catalyst. For example, a complex of 1,1,3,3-tetramethyl-1,3-divinyldisiloxane and chloroplatinic acid neutralized with sodium bicarbonate (Karstedt's catalyst) is more preferred.

The amount of the hydrosilylation catalyst may be a catalytic amount sufficient to promote the aforesaid reaction. For example, the complex of 1,1,3,3-tetramethyl-1,3-divinyldisiloxane and chloroplatinic acid neutralized with sodium bicarbonate may be used in an amount such that the amount of platinum is 1 to 80 ppm, based on the mass of the hydrogen siloxane compound represented by the formula (6) or (7).

Examples of the solvent include glycol ether solvents such as methyl cellosolve, ethyl cellosolve, isopropyl cellosolve, butyl cellosolve, propylene glycol monomethyl ether, diethylene glycol monomethyl ether, triethylene glycol monomethyl ether, polyethylene glycol monomethyl ether, ethylene glycol dimethyl ether, diethylene glycol dimethyl ether, triethylene glycol dimethyl ether, and polyethylene glycol dimethyl ether; ester-based solvents such as ethyl acetate, butyl acetate, amyl acetate, ethyl lactate, and methyl benzoate; aliphatic hydrocarbon-based solvents such as linear hexane, linear heptane, and linear octane; alicyclic hydrocarbon-based solvents such as cyclohexane and ethylcyclohexane; ketone-based solvents such as acetone, methyl ethyl ketone, and methyl isobutyl ketone; aromatic hydrocarbon solvents such as benzene, toluene, and xylene; petroleum-based solvents; and alcohol-based solvents such as methyl alcohol, ethyl alcohol, linear propyl alcohol, isopropyl alcohol, linear butyl alcohol, isobutyl alcohol, tert-butyl alcohol, ethylene glycol, diethylene glycol, triethylene glycol, tetraethylene glycol, and polyethylene glycol. The aforesaid solvents may be used either alone or in combination of two or more.

Examples of the stabilizer include phenolic antioxidants, phosphorus-based antioxidants, amine-based antioxidants, and sulfur-based antioxidants. Any phenolic antioxidant may be used, and includes compounds selected from p-methoxyphenol, di-tert-butyl-p-cresol, pyrogallol, tert-butylcatechol, 4,4-thiobis(3-methyl-6-tert-butylphenol), 2,2'-methylenebis(4-methyl-6-t-butylphenol), phenolic resins and cresol resins. The phosphorus-based antioxidant is not particularly limited, and includes tris[2-[[2,4,8,10-tetrakis(1,1-dimethylethyl)dibenzo[d,f][1,3,2]dioxaphosphepin-6-yl]oxy]ethyl]amine, tris[2-[(4,6,9,11-tetra-tert-butyldibenzo[d,f][1,3,2]dioxaphosphepin-2-yl)oxy]ethyl]amine, and ethylbis(2,4-ditert-butyl-6-methylphenyl)phosphite. The amine-based antioxidant is not particularly limited, and includes tri- or tetra-$C_{1-3}$ alkylpiperidines and derivatives thereof, bis(2,2,6,6-tetramethyl-4-piperidyl)oxalate, 1,2-bis(2,2,6,6-tetramethyl-4-piperidyloxy)ethane, phenylnaphthylamine, N,N'-diphenyl-1,4-phenylenediamine, and N-phenyl-N'-cyclohexyl-1,4-phenylenediamine. The sulfur-based antioxidant is not particularly limited and includes dilaurylthiodipropionate and distearylthiodipropionate. The stabilizer may be used alone or in combination thereof.

In each of the aforesaid reactions, the end point of the reaction may be known by disappearance of a peak of a raw material compound in a conventional method, for example, by thin-layer chromatography (TLC), high-speed liquid chromatography (HPLC), or gas chromatography (GC). After completion of the reaction, purification may be conducted in any conventional method. For example, an organic layer is washed with water and a solvent is removed to obtain a product. Alternatively, distillation at a reduced pressure or treatment with activated carbon may be conducted.

A method for preparing the unsaturated group-containing compound represented by the aforesaid formula (5) is not particularly limited. The unsaturated group-containing compound may be obtained, for example, by reacting an epoxy compound represented by the following formula (a) with a (meth)acrylic acid.

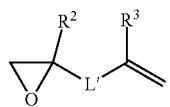
(a)

wherein $R^2$, $R^3$ and L' are as described above.

A method for preparing the compound represented by the aforesaid formula (a) may be any conventional manner. For example, an epoxy compound represented by the aforesaid formula (a), having 2 to 8 carbon atoms and L' having one or more ether bonds are obtained by reacting an alcohol compound represented by the following formula (4):

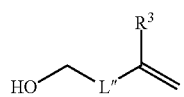
(4)

wherein $R^3$ is as described above and L" is a single bond or a divalent hydrocarbon group which has 1 to 6 carbon atoms and may have ether bond(s), with an epoxy compound represented by the following formula (5):

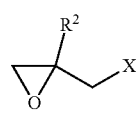
(5)

wherein $R^2$ is as described above and X is a halogen atom.

The reaction between the aforesaid alcohol compound and the epoxy compound may be conducted in accordance with any conventional manner. For example, 1 molar equivalent or more of the epoxy compound and 1 molar equivalent of the alcohol compound are put together and be subjected to the reaction. The reaction temperature is not particularly limited, but is preferably not higher than a boiling temperature of a solvent used. For example, the reaction temperature is preferably about 0° C. to about 120° C. The aforesaid reaction may be conducted in the presence of a solvent and a catalyst. The solvent and catalyst are not particularly limited and any known ones.

The reaction of the epoxy compound represented by the formula (a) with (meth)acrylic acid may be done in any known manner. For example, 1 molar equivalent of the epoxy compound and 1 molar equivalent or more of (meth)acrylic acid may be subjected to the reaction. A reaction temperature is not particularly limited, and is preferably a temperature not exceeding a boiling temperature of a solvent to be used. For example, the reaction temperature is preferably from about 0° C. to about 110° C. The reaction may be done in the presence of a solvent, a catalyst and a stabilizer. Any known solvent, catalyst and stabilizer may be used. The solvent may be those described above.

Examples of the catalyst include organometallic catalysts, basic compounds, organophosphorus-based compounds, amine catalysts, and Lewis acids. Examples of the stabilizers include phenolic antioxidants, phosphorus-based antioxidants, amine-based antioxidants, and sulfur-based antioxidants. Specific examples are as described above.

In an embodiment of the preparation method of the present invention, 1 molar equivalent of the hydrogen siloxane compound represented by the formula (6) or (7), 1.5 molar equivalents of the unsaturated compound represented by the aforesaid formula (5), a solution of a complex of chloroplatinic acid neutralized with sodium bicarbonate and vinyl siloxane in toluene (platinum content: 0.5 wt %) in an amount of 10 ppm of platinum, based on the mass of the polysiloxane compound, and 0.1 mass % of toluene, based on the hydrogen siloxane compound, are put together and stirred at 80° C. in a nitrogen atmosphere to be allowed to react for about 2 hours, whereby the reaction is completed. The progress of the reaction may be followed by monitoring the unsaturated compound or a formed compound by GC. After completion of the reaction, n-hexane is added in an amount of 100 mass %, based on the hydrogen siloxane compound, and the organic layer is separated and washed with aqueous methanol (methanol:water=4:1). Then, the solvent and the unreacted raw material present in the organic layer are distilled off at a reduced pressure to obtain a siloxane compound represented by the aforesaid formula (1).

The compound of the present invention may be converted into a polymer comprising the retuning unit derived from the addition polymerization at the (meth)acrylic group. The compound of the present invention has good compatibility with another compound having a polymerizable group such as (meth)acrylic group (hereinafter referred to as "a polymerizable monomer" or "a hydrophilic monomer"). A copolymer with the polymerizable monomer is therefore colorless and transparent. Alternatively, the compound of the present invention may be homo-polymerized.

In the preparation of the copolymer comprising the recurring units derived from the polymerization of the compound of the present invention and from the another polymerizable (or hydrophilic) monomer, the amount of the compound of the present invention may be such that the mass of the recurring unit is at least 10% by mass, based on the mass of the copolymer. More specifically, the amount of the compound of the present invention may be 10 to 80 parts by mass, more preferably 10 to 60 parts by mass, relative to total 100 parts by mass of the compound of the invention and the polymerizable (hydrophilic) monomer. If the mass percent of the recurring unit is less than 10%, the resulting copolymer is unlikely to exhibit the properties of the present compound.

Examples of the polymerizable monomer include acrylic monomers such as (meth)acrylic acid, methyl(meth)acrylate, ethyl(meth)acrylate, (poly)ethylene glycol dimethacrylate, polyalkylene glycol mono(meth)acrylate, polyalkylene glycol monoalkyl ether (meth)acrylate, trifluoroethyl (meth) acrylate, 2-hydroxyethyl (meth)acrylate, and 2,3-dihydroxypropyl (meth)acrylate; acrylic acid derivatives such as N,N-dimethylacrylamide, N,N-diethylacrylamide, N-acryloylmorpholine, and N-methyl (meth)acrylamide; N-vinylpyrrolidone, and other unsaturated aliphatic or aromatic compounds such as crotonic acid, cinnamic acid, and vinylbenzoic acid; and siloxane monomers having a polymerizable group such as (meth)acrylic group. The monomer may be used alone or in combination thereof.

The copolymerization of the compound of the present invention with the another polymerizable monomer may be conducted in any conventional manner, for example, in the presence of a known polymerization initiator such as a heat polymerization initiator or a photopolymerization initiator. Examples of the polymerization initiator include 2-hydroxy-2-methyl-1-phenyl-propan-1-one, azobisisobutyronitrile, azobisdimethylvaleronitrile, benzoyl peroxide, tert-butyl hydroperoxide, cumene hydroperoxide, and 2,2'-azobis(2-methylpropionamidine) dihydrochloride. The polymerization initiator may be used alone or in combination thereof. An amount of the polymerization initiator is preferably from 0.001 to 2 parts by mass, more preferably from 0.01 to 1 part by mass, per total 100 parts by mass of the components to be polymerized.

The polymer comprising the recurring unit derived from the compound of the present invention is excellent in hydrophilicity. The hydrogel obtained from the polymer is excellent in transparency and strength. The compound of the present invention is therefore suited for use in the preparation of medical materials such as ophthalmic devices, contact lenses, intraocular lenses, and artificial corneas. The method of preparing a medical material from the polymer is not particularly limited and may be any conventional method. For example, a cutting process or a molding process may be used for shaping the polymer into a lens, such as contact lens or intraocular lens.

EXAMPLES

The present invention will hereinafter be described more specifically with reference to the following Examples and Comparative Examples, but the present invention is not limited by the following Examples. In the following Examples, $^1$H-NMR analysis was done with JEOL ECS400 using deuterated chloroform as a measurement solvent. The gas chromatography (GC) was conducted in the following conditions.

Measuring apparatus: Gas Chromatograph FID detectorex Agilent

Capillary column: HP-5MS (0.25 mm×30 m×0.25 µm), ex J&W

Heating program: 50° C. (5 minutes)→10° C./min→250° C. (held)

Injector temperature at the injection port: 250° C., and an FID detector temperature: 300° C.

Carrier gas: helium (1.0 ml/min)

Split ratio: 50:1, injected volume: 1 µL

The following compounds were used in the following Examples and Comparative Examples.

AHMPM:
3-(allyloxy)-2-hydroxy-2-methylpropylmethacrylate

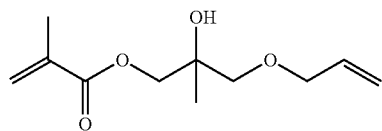

AHPM: 3-(allyloxy)-2-hydroxypropyl methacrylate

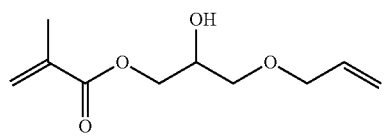

SiGMA: methyl bis(trimethylsiloxy)silylpropylglycerol methacrylate

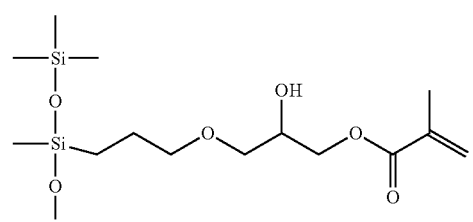

(a)

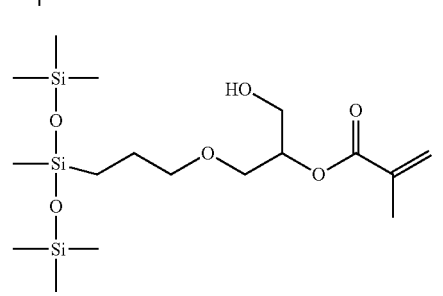

(a')

Example 1

In a 300-mL three-necked eggplant flask equipped with a Dimroth condenser and a thermometer, were added 50.0 g of 1,1,1,3,5,5,5-heptamethyltrisiloxane, 72.0 g of AHMPM (thus, a molar ratio of the unsaturated compound to the hydrogen siloxane compound is 1.5), and 0.03 g of a solution of a complex of chloroplatinic acid neutralized with sodium bicarbonate and vinyl siloxane in toluene platinum content: 0.5 wt %) in a nitrogen atmosphere. The resulting mixture was heated to 80° C. and aged for 4 hours. After completion of the reaction, 50.0 g of n-hexane was added and the resulting mixture was washed five times with an aqueous methanol solution (methanol:water=4:1). The solvent and the unreacted raw materials were distilled off at a temperature of 80° C. and a reduced pressure to obtain a colorless, transparent liquid. The yield was 62.5 g. According to $^1$H-NMR, the liquid was a compound represented by the following formula (9).

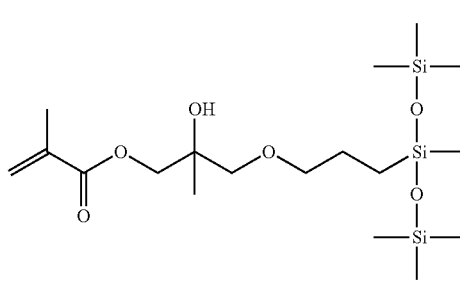

(9)

The $^1$H-NMR data are as follows.
0.0-0.1 ppm(21H), 0.4 ppm(2H), 1.2 ppm(3H), 1.6 ppm (2H), 2.0 ppm(3H), 3.3-3.4 ppm(4H), 4.1 ppm(2H), 5.6 ppm(1H), 6.1 ppm(1H)

Example 2

The procedures of Example 1 were repeated, except that 50.0 g of a hydrogen siloxane compound represented by the following formula (10A) was used instead of 1,1,1,3,5,5,5-heptamethyltrisiloxane used in Example 1 and the amount of AHMPM was changed to 51.4 g (thus, a molar ratio of the unsaturated compound to the hydrogen siloxane compound is 1.5) to thereby obtain a colorless, transparent liquid. The yield was 69.0 g. According to $^1$H-NMR, the liquid was a compound represented by the following formula (10B).

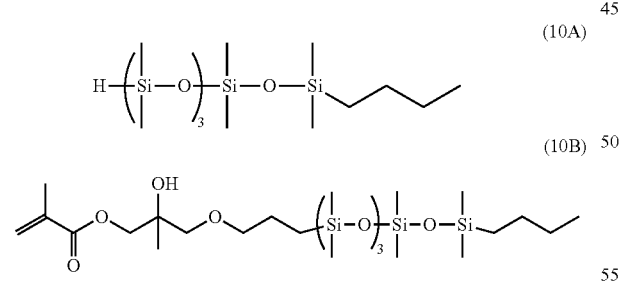

(10A)

(10B)

The data are as follows.
0.0-0.1 ppm(30H), 0.5 ppm(4H), 0.9 ppm(3H), 1.2 ppm (3H), 1.3 ppm(4H), 1.6 ppm(2H), 2.0 ppm(3H), 3.3-3.4 ppm(4H), 4.1 ppm(2H), 5.6 ppm(1H), 6.1 ppm(1H)

Example 3

The procedures of Example 1 were repeated, except that 50.0 g of a hydrogen siloxane compound represented by the following formula (11A) was used instead of 1,1,1,3,5,5,5-heptamethyltrisiloxane used in Example 1 and the amount of AHMPM was changed to 10.6 g (thus, a molar ratio of the unsaturated compound to the hydrogen siloxane compound is 1.5) to obtain a colorless, transparent liquid. The yield was 70.5 g. According to $^1$H-NMR, the liquid was a compound represented by the following formula (11B).

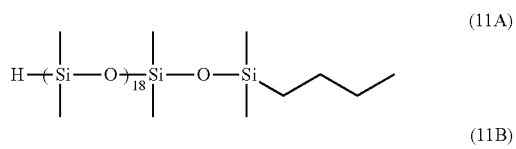

(11A)

(11B)

The $^1$H-NMR data are as follows.
0.0-0.1 ppm(120H), 0.5 ppm(4H), 0.9 ppm(3H), 1.2 ppm (3H), 1.3 ppm(4H), 1.6 ppm(2H), 2.0 ppm(3H), 3.3-3.4 ppm(4H), 4.1 ppm(2H), 5.6 ppm(1H), 6.1 ppm(1H)

Evaluation of the Reactivity of the Unsaturated Group-Containing Compound which was a Raw Material Examples 4 to 9 and Comparative Example 1

The hydrogen siloxane compound represented by the aforesaid formula (10A), the following AHMPM (tertiary hydroxyl group-containing compound) or the following AHPM (secondary hydroxyl group-containing compound), and a solution of a complex of chloroplatinic acid neutralized with sodium bicarbonate and vinyl siloxane in toluene (platinum content: 0.5 wt %) were mixed in the amounts described in Table 1. The resulting mixture was heated to 80° C. in a nitrogen atmosphere and aged for 4 hours. After completion of the reaction, the reaction mixture was subjected to GC analysis and the purity of the intended product was calculated from the area %, provided that any remaining raw materials, hydrogen siloxane compound, AHMPA, and AHPM, were neglected in the calculation of the purity. The results are as shown in Table 1.

AHMPM: 3-(allyloxy)-2-hydroxy-2-methylpropyl methacrylate

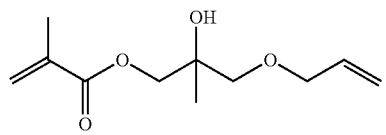

AHPM: 3-(allyloxy)-2-hydroxypropyl methacrylate

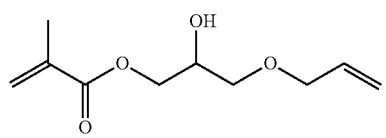

TABLE 1

|  |  | Ex. 4 | Ex. 5 | Ex. 6 | Ex. 7 | Ex, 8 | Ex. 9 | Com Ex. 1 |
|---|---|---|---|---|---|---|---|---|
| Compound represented by the formula (10A) | molar ratio | 1 | 1 | 1 | 1 | 1 | 1 | 1 |
| AHMPM, Tertiary hydroxyl group-containing compound | molar ratio | 0.8 | 1 | 1.2 | 1.5 | 2 | 3 | — |
| AHPM, Secondary hydroxyl group-containing compound | molar ratio | — | — | — | — | — | — | 1.5 |
| Solution of a complex of chloroplatinic acid neutralized with sodium bicarbonate and vinyl siloxane in toluene | part by mass | 0.05 | 0.05 | 0.05 | 0.05 | 0.05 | 0.05 | 0.05 |
| Purity | % | 81.4 | 91 | 92.7 | 94.3 | 95.2 | 95.6 | 91.6 |

As seen in Table 1, when the molar ratio of AHMPM having a tertiary hydroxyl group to the hydrogen siloxane compound is 1.0 or more in the addition reaction, the intended compound has a particularly improved purity. A side reaction during the hydrosilylation reaction is suppressed, which further increases the purity. In contrast, the compound obtained in Comparative Example 1 by the addition reaction of the unsaturated group-containing compound (AHPM) having a secondary hydroxyl group and the hydrogen siloxane has a lower purity, compared to the compound of Example 7 prepared in the same molar ratio. This result means that any side reaction occurred more during the hydrosilylation reaction in Comparative Example 1.

Examples 10 to 14 and Comparative Examples 2 to 4

Preparation of a Hydrogel

The compounds obtained in the aforesaid Examples 1 to 3, SiGMA represented by the following formula, 3-[tris (trimethylsiloxy)silyl]propyl methacrylate (TRIS) represented by the following formula, 2-hydroxyethyl methacrylate (HEMA), N,N-dimethylacrylamide (DMA), ethylene glycol dimethacrylate (EGDMA), and Irgacure1173 (Irg1173) were mixed in the composition and the ratios shown in Table 2 or 3 and stirred until the mixture became a uniform solution. After the stirring, bubbling with $N_2$ was carried out for 5 minutes for sufficient deaeration and, then, the solution was put in a mold made of polypropylene and the mold was sealed. The mold containing the solution was irradiated with UV with a high-pressure mercury lamp to cure the solution. After the curing, a resulting resin was taken out from the mold and immersed in isopropanol, a 50% aqueous solution of isopropanol and then deionized water for washing to obtain a hydrogel film. Physical properties of the film thus obtained were determined in the method described below. The results are as shown in Tables 2 and 3.

SiGMA: methylbis(trimethylsiloxy)silylpropylglycerol methacrylate

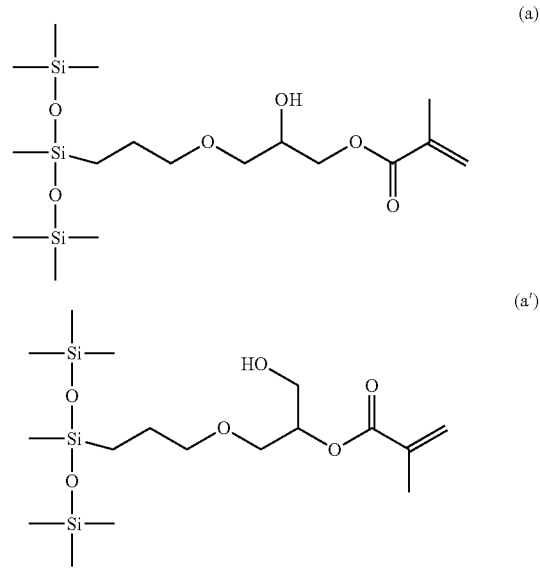

TRIS: 3-[tris(trimethylsiloxy)silyl]propyl methacrylate

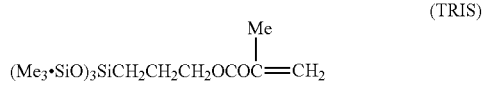

Equilibrium Water Content

The film was immersed in deionized water at 25° C. for 48 hours, water on the film surface was wiped off, and the mass of the hydrated film was measured. Then, the hydrated film was dried in an oven at 50° C. for 48 hours and then at 25° C. for 24 hours and the mass of the dried film was measured. The equilibrium water content was calculated according to the following formula:

Equilibrium water content (%)=100×[{(mass of the hydrated film)−(mass of the dried film)}/(mass of the hydrated film)]

Transparency

The film was immersed in deionized water at 25° C. for 48 hours and water on the film surface was wiped off to prepare a hydrated film. The appearance of the hydrated film was visually evaluated, based on the following criteria:
A: the film is uniform and transparent.
B: the film is non-uniform or cloudy.

Modulus of Elasticity

The film was immersed in deionized water at 25° C. for 48 hours, water on the film surface was wiped off to prepare a hydrated film. A Young's modulus of elasticity of the hydrated film was determined using Instron 5943, as follows. A sample piece of 0.8 cm×4.0 cm obtained by cutting the hydrated film was stretched with a load cell of 50 N at a head speed of 1 cm/min to obtain a curve of the stress in the ordinate and the strain in the abscissa. A slope of a stress-strain curve in the initial linear stage was determined. The slope is a Young's modulus of elasticity in MPa.

TABLE 2

|  |  | Example 10 | Example 11 | Example 12 | Example 13 | Example 14 |
|---|---|---|---|---|---|---|
| Siloxane | 9 | 10 | 50 | 0 | 0 | 0 |
| Compound | 10B | 0 | 0 | 10 | 50 | 0 |
|  | 11B | 0 | 0 | 0 | 0 | 50 |
| Comparative | SiGMA | 0 | 0 | 0 | 0 | 0 |
| Compound | TRIS | 40 | 0 | 40 | 0 | 0 |
| Polymerizable | HEMA | 10 | 10 | 10 | 10 | 10 |
| monomer | DMA | 38 | 38 | 38 | 38 | 38 |
|  | EGDMA | 1 | 1 | 1 | 1 | 1 |
|  | IRG1173 | 1 | 1 | 1 | 1 | 1 |
| Evaluation | Equilibrium water content, % | 46 | 53 | 45 | 53 | 50 |
|  | Transparency | A | A | A | A | A |
|  | Elastic Modulus, MPa. | 0.41 | 0.42 | 0.44 | 0.37 | 0.35 |

TABLE 3

|  |  | Comparative Example 2 | Comparative Example 3 | Comparative Example 4 |
|---|---|---|---|---|
| Siloxane | 9 | 0 | 0 | 0 |
| Compound | 10B | 0 | 0 | 0 |
|  | 11B | 0 | 0 | 0 |
| Comparative | SiGMA | 0 | 10 | 50 |
| Compound | TRIS | 50 | 40 | 0 |
| Polymerizable | HEMA | 10 | 10 | 10 |
| monomer | DMA | 38 | 38 | 38 |
|  | EGDMA | 1 | 1 | 1 |
|  | IRG1173 | 1 | 1 | 1 |
| Evaluation | Equilibrium water content, % | 45 | 47 | 55 |
|  | Transparency | B | A | A |
|  | Elastic Modulus, MPa | 0.43 | 0.53 | 0.51 |

As seen in Table 3, the hydrogel prepared with TRIS only as a comparative compound has the poor transparency (Comparative Example 2). The hydrogels prepared with SiGMA only or the combination of SiGMA and TRIS as a comparative compound show the too high modulus of elasticity (Comparative Examples 3 and 4).

In contrast, as seen in Table 2, the hydrogel prepared with the siloxane compound of the present invention has excellent transparency and the proper modulus of elasticity. Thus, the hydrogel obtained using the compound of the present invention has both of the useful hydrophilicity and the sufficient strength.

INDUSTRIAL APPLICABILITY

The hydrogel obtained using the compound of the present invention has improved hydrophilicity and strength. The compound of the present invention is useful as a monomer to prepare medical materials such as ophthalmic devices, contact lenses, intraocular lenses, artificial corneas and eyeglass lenses.

The invention claimed is:
1. A siloxane represented by the following formula (1):

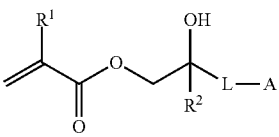

(1)

wherein $R^1$ is a hydrogen atom or a methyl group, $R^2$ is a monovalent hydrocarbon group having 1 to 6 carbon atoms, L is a divalent hydrocarbon group which has 2 to 10 carbon atoms and may have one or more ether bonds, and A is a group represented by the following formula (2) or (3):

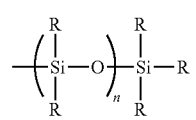

(2)

-continued

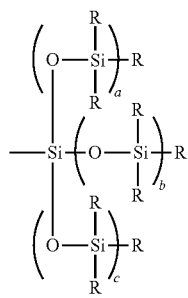
(3)

wherein n is an integer of 1 to 100, a is an integer of 0 to 10, b is an integer of 0 to 10, and c is an integer of 0 to 10, provided that a+b+c is 2 or more, and R is, independently of each other, a monovalent hydrocarbon group having 1 to 10 carbon atoms.

2. The siloxane according to claim 1, wherein L is a divalent group represented by the following formula (4):

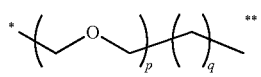
(4)

wherein p is an integer of 1 to 2, q is an integer of 1 to 4, the site marked with * is bonded to the carbon atom in the formula (1) and the site marked with ** is bonded to A in the formula (1).

3. The siloxane according to claim 2, wherein p is 1, and q is 2.

4. The siloxane according to claim 1, wherein A is represented by the formula (2) and n is an integer of 2 to 20 in the formula (1).

5. The siloxane according to claim 1, wherein A is represented by the formula (3), wherein a is 1, b is 1 and c is 0.

6. The siloxane according to claim 1, wherein $R^2$ in the formula (1) is a methyl group.

7. The siloxane according to claim 1, wherein R in the formula (2) or (3) is, independently of each other, an alkyl group having 1 to 6 carbon atoms or a phenyl group.

8. The siloxane according to claim 7, wherein R is, independently of each other, a methyl, n-butyl or t-butyl group.

9. A polymer comprising recurring units derived from polymerization at the (meth)acryl group of the siloxane according to claim 1.

10. The polymer according to claim 9, wherein an amount of the recurring units is 10 mass % or more, based on a mass of the polymer.

11. A hydrogel comprising the polymer according to claim 9.

12. A medical material comprising the polymer according to claim 9.

13. A method for preparing a siloxane represented by the following formula (1):

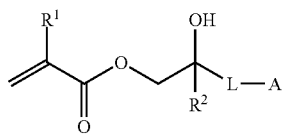
(1)

wherein $R^1$ is a hydrogen atom or a methyl group, $R^2$ is a monovalent hydrocarbon group having 1 to 6 carbon atoms, L is a divalent hydrocarbon group which has 2 to 10 carbon atoms and may have one or more ether bonds, and A is a group represented by the following formula (2) or (3):

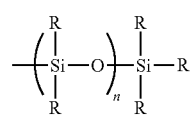
(2)

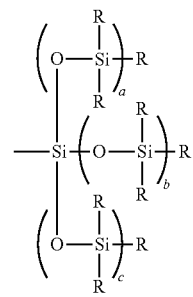
(3)

wherein n is an integer of 1 to 100, a is an integer of 0 to 10, b is an integer of 0 to 10, and c is an integer of 0 to 10, provided that a+b+c is 2 or more, and R is, independently of each other, a monovalent hydrocarbon group having 1 to 10 carbon atoms, the method comprises a step of hydrosilylation-reacting a compound represented by the following formula (5) and having unsaturated groups at the terminals:

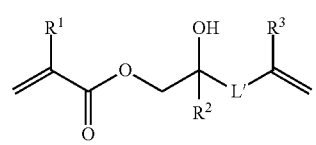
(5)

wherein $R^1$ and $R^2$ are as defined above, $R^3$ is a hydrogen atom or a methyl group, and L' is a single bond or a divalent hydrocarbon group which has 1 to 8 carbon atoms and may have one or more ether bonds, with a hydrogen siloxane represented by the following formula (6) or (7):

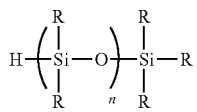
(6)

(7)

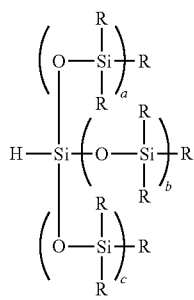

wherein R, n, a, b and c are as defined above, to obtain the siloxane represented by the aforesaid formula (1).

14. The method according to claim 13, wherein a molar ratio of the unsaturated group-containing compound to the hydrogen siloxane is 1.0 to 3.0.

15. The method according to claim 13, wherein L is a divalent group represented by the following formula (4):

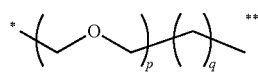

(4)

wherein p is an integer of 1 to 2, q is an integer of 1 to 4, the site marked with * is bonded to the carbon atom in the formula (1) and the site marked with ** is bonded to A in the formula (1).

16. The method according to claim 13, wherein A is represented by the formula (2) and n is an integer of 2 to 20.

17. The method according to claim 13, wherein A is represented by the formula (3), wherein a is 1, b is 1, and c is 0.

18. The method according to claim 13, wherein $R^2$ is a methyl group.

19. The method according to claim 13, wherein R is, independently of each other, an alkyl group having 1 to 6 carbon atoms or a phenyl group.

20. The method according to claim 19, wherein R is, independently of each other, a methyl, n-butyl or t-butyl group.

* * * * *

UNITED STATES PATENT AND TRADEMARK OFFICE
CERTIFICATE OF CORRECTION

PATENT NO. : 12,180,310 B2
APPLICATION NO. : 17/616388
DATED : December 31, 2024
INVENTOR(S) : Kaoru Okamura Page 1 of 1

It is certified that error appears in the above-identified patent and that said Letters Patent is hereby corrected as shown below:

In the Specification

Column 11, Line 57: Please correct "The data" to read --The $^1$H-NMR data--

In the Claims

Column 17, Line 55, Claim 9: Please correct "(meth)acry l group" to read --(meth)acryl group--

Signed and Sealed this
Sixth Day of May, 2025

Coke Morgan Stewart
*Acting Director of the United States Patent and Trademark Office*